(12) United States Patent
Walczyk et al.

(10) Patent No.: US 6,405,606 B1
(45) Date of Patent: Jun. 18, 2002

(54) MECHANICAL WEIGHT BEARING INDICATOR FOR THE FOOT

(75) Inventors: Daniel F. Walczyk, Brunswick, NY (US); Amy E. Kerdok, Somerville, MA (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 09/126,271

(22) Filed: Jul. 30, 1998

Related U.S. Application Data

(60) Provisional application No. 60/054,478, filed on Aug. 1, 1997.

(51) Int. Cl.[7] .............................. G01L 1/00; A61B 5/00; A43B 23/00
(52) U.S. Cl. .................. 73/862.381; 73/172; 36/136
(58) Field of Search .......................... 73/172, 862.381, 73/862.041–862.046, 818–825; 36/136, 113, 8.3, 139, 114; 340/373, 272; 116/240, 200, 203, 205, 101, 212; 177/239, 245, 264; 446/176, 180, 181, 184, 185, 188, 193, 196, 197, 213, 404

(56) References Cited

U.S. PATENT DOCUMENTS

| | | | | |
|---|---|---|---|---|
| 3,340,846 A | * | 9/1967 | Magiera | 116/67 R |
| 4,513,519 A | * | 4/1985 | Hedrick | 36/113 |
| 4,625,436 A | * | 12/1986 | Stevens, Jr. | 36/113 |
| 4,925,425 A | * | 5/1990 | Ohta et al. | 446/185 |
| 5,060,527 A | * | 10/1991 | Burgess | 73/862.68 |
| 5,269,081 A | * | 12/1993 | Gray | 36/136 |
| 5,648,617 A | * | 7/1997 | Cullen et al. | 73/862.045 |
| 5,712,452 A | * | 1/1998 | Lin | 180/0.5 |

* cited by examiner

Primary Examiner—Benjamin R. Fuller
Assistant Examiner—Abdullahi Aw-Musse
(74) Attorney, Agent, or Firm—Notaro & Michalos P.C.

(57) ABSTRACT

A mechanical weight bearing indicator produces a tactile signal which is felt by the wearer's foot. The signal is generated when the user exerts more than a predetermined amount of weight on the indicator, giving the user, who may be an orthopedic patient, immediate feedback concerning the amount of force applied. The indicator automatically resets and has no power source, but is purely mechanical. In one version of the invention, a domed metal disk is used as part of the indicator which snaps from a stable position to an unstable position in the way the bottom of an oil can operates, to produce the tactile signal and also for producing a sound as an audible signal. In another version of the invention, a piston and cylinder are used with the piston moving under the influence of a threshold of pressure exerted by the deformation of a compressible cavity member on which the user steps. The threshold pressure in the compressible cavity member is reached when a one-way, force-actuated release valve is activated.

1 Claim, 3 Drawing Sheets

MECHANICAL WEIGHT BEARING INDICATOR FOR THE FOOT

CROSS-REFERENCE TO RELATED APPLICATION

The present application claims the benefit of Provisional Application No. 60/054,478, filed Aug. 1, 1997, which is incorporated herein by reference.

FIELD AND BACKGROUND OF THE INVENTION

The present invention relates, in general, to force indicators, and in particular, to a new and useful weight bearing indicator which is purely mechanical and simple yet provides an unambiguous message to a person wearing the indicator that a set amount of force between the person's foot and the ground has been exceeded.

Following orthopedic surgery or injury to the lower extremities, patients are encouraged to exercise but are warned not to exert more than a certain limited amount of force on the injured lower extremity.

As a result, most patients do not apply any weight or apply insufficient weight to the injured lower extremity in fear of causing further damage. The application of weight is necessary, however, for proper recovery and not applying any weight is almost as detrimental as applying too much weight. A survey was conducted at Albany Medical College (Albany, N.Y.) involving over 100 patients. The patients indicated that often no weight was applied to the injured foot.

Electrical and electronic devices are known which sense the force applied to a foot and provide a signal to the wearer. See, for example, U.S. Pat. No. 5,408,873 which discloses a foot force sensor and U.S. Pat. No. 5,357,696 which discloses a device for measuring force applied to a wearer's foot. The following additional patents, listed by patent number and title, are also relevant:

| U.S. Pat. No. | TITLE OF INVENTION |
| --- | --- |
| 5,619,186 | Foot Weight Alarm |
| 5,323,650 | System for Continuously Measuring Forces Applied to the Foot |
| 5,269,081 | Force Monitoring Shoe |
| 5,253,654 | Orthopedic Weight Monitor |
| 4,858,620 | Warning System for Excessive Orthopedic Pressures |
| 4,814,661 | Systems for Measurement and Analysis of Forces Exerted During Human Locomotion |
| 4,745,930 | Force Sensing Insole for Electro-Goniometer |
| 4,647,918 | Multi-event Notification System for Monitoring Critical Pressure Points on Persons with Diminished Sensation of the Foot |
| 3,974,491 | Load Signaling Device for a Patient's Foot |
| 3,791,375 | Device for Sensing and Warning of Excessive Ambulation Force |
| 3,702,999 | Partial Weight Bear Warning Device |

An electronic weight bearing alarm is also available under the trademark PEDALERT from Sammons Preston. This device monitors the amount of weight a patient places on his or her lower limb through an advanced membrane sensor. An audible beep warning is generated when the weight limit is exceeded.

The need remains for a simple mechanical device which produces-an unmistakable feedback signal to only the patient which is preferably mechanical, but which may also include an audible sound, and which can be in the shoe.

SUMMARY OF THE INVENTION

An object of the present invention is to provide a simple mechanical device which produces a tactile and in one embodiment, a tactile and audible feedback signal applied directly to the foot of the patient who wears the device in his or her shoe, sandle or other foot covering.

The device of the present invention resets automatically and requires no power source and thus is non-electric. Accordingly, there are no batteries to run down and no recharge required to maintain the usefulness of the invention for long periods of time.

A patient recovering from lower extremity injuries, surgery or other conditions such as a neurological patients, athletes and the like, simply inserts the device of the present invention into his or her shoe, under a particular area of the foot depending on the embodiment of the invention, and wears the shoe in a normal fashion. The present invention can also be incorporated into an orthotic device or cast worn by the patient on their foot.

The invention is a purely mechanical device which senses, in one embodiment, and reacts to, in another embodiment how much weight is being applied through it, that is, between the bottom of the patient's foot and the ground, and indicates to the patient when this level is above a preselected value, e.g., the maximum weight permitted at the particular stage of the patient's recovery.

According to one embodiment of the invention, a pressurized chamber is used in the device which produces a momentary tactile indication to the bottom of the wearer's foot when the device receives more than a preselected amount of force. According to another embodiment, a so-called snap-through buckling device produces the tactile and in this case, also an audible indication in the form of a click sound.

All embodiments of the invention are reusable and automatically reset. In this way, the patient is provided with ongoing feedback on the amount of force he or she may apply to the injured area. If the set force is exceeded, the tactile sensation (and audible feedback with one embodiment) will be felt (and heard) and the patient will know to apply less force on the next step. The ability of the device to reset instantly is also essential so that the patient's normal activities are not interrupted and the patient is also encouraged to apply as much force as possible to advance healing, without exceeding the force on a regular basis. In effect, the patient learns how much force to apply. According to the invention, the device can be configured to provide indications at different loads so that the patient can be permitted to exert higher force as the healing process continues. This is achieved simply by switching components (spring disk, coil spring or reaction plate) in each embodiment of the present invention to allow succeeding increased force limits.

Another advantage of the invention is that the feedback signal, including the audible sound, is perceptible, generally only by the patient so that no attention is drawn to the patient or the patient's condition.

In addition to its therapeutic value, the present invention is also a simple device for use in athletics, physical therapy, gait analysis and the like, wherever a set force limit is desirable or not desirable for applying between a part of the body and another surface.

Thus, a still further object of the present invention is to provide a mechanical weight bearing indicator for producing a signal to a user when the user applies more than a selected amount of weight between an extremity of the use and a surface, comprising a reaction plate adapted to establish a frame of reference with the surface; an actuator plate mounted for movement to said reaction plate and adapted to receive weight from the user's extremity; and purely mechanical indicator means operatively connected to said actuator plate for generating a tactile signal directly to the extremity when more than the selected amount of weight is applied to said reaction plate by the extremity.

A still further object of the present invention is to provide a mechanical weight bearing indicator which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Connected between the actuator plate and the reaction plate 12, 14, is a purely mechanical indicator means according to the present invention generally designated 18 and operatively connected to the actuator plate.

Figure 1:
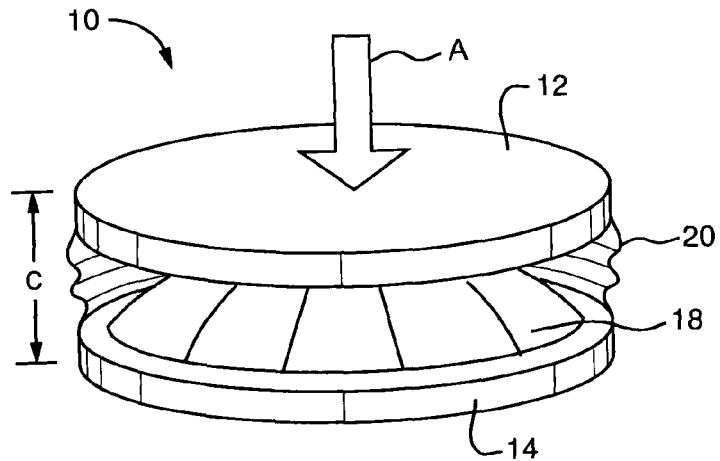
FIG. 1 is a perspective view of a first embodiment of the invention which produces an audible and tactile indication to a person wearing the device.
Figure 2A:
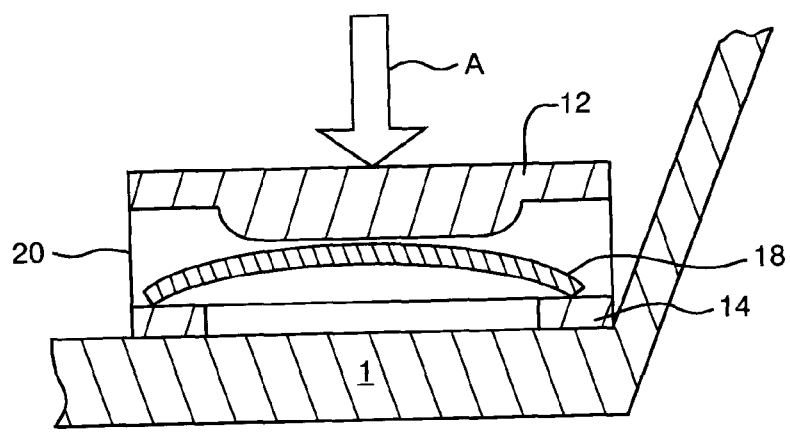
FIG. 2A is a sectional view of the embodiment of FIG. 1 showing the device prior to generation of the device signal.
Figure 2B:
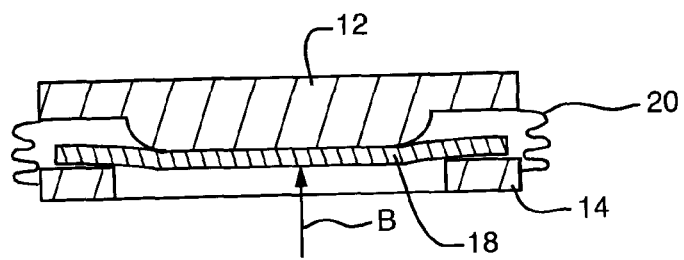
FIG. 2B is a view similar to FIG. 2A, immediately after it has generated the signal.

In the embodiment of FIG. 1, the indicator means 18 is a thin convex or dome-shaped disk of spring metal or plastic which is shown in its stable condition in FIGS. 1 and 2A, and in a snap-through unstable condition in FIG. 2B. Disk 18 operates in the same way as the bottom of an oil can. If sufficient downward force in the direction of arrow A in FIGS. 1 and 2A is exerted, the dome-shaped spring disk 18 (e.g., made of tempered spring steel,) will snap or buckle into its unstable position shown in FIG. 2B, becoming now upwardly concave. If the force is removed, a restoring internal force, from a build-up of internal material strains, in the direction of arrow B in FIG. 2B will cause member 18 to return to its upwardly dome-shaped position of FIG. 1. The upper plate 12 and lower plate 14 are made of any suitable material, for example, hard ABS plastic, metal or the like, with the lower plate 14 containing a large opening for receiving the disk 18 and permitting its free movement between its stable and unstable conditions.

Plates 12, 14 are approximately 4 to 6 cm in diameter to roughly correspond to the size of a human heel. Varying thicknesses, material and geometry (i.e., radius of curvature, height, diameter) of the disk 18 can be selected so that it buckles to its unstable condition under different, but specifically selected, forces corresponding to maximum weights permitted for the user's heel. The material of disk 18 may be any spring-like metal such as steel or other metal alloy, having high tensile strength, or may be plastic or elastomer capable of having the stable and unstable positions, such as nylon. The overall height of the device 10 shown at C in FIG. 1 should be approximately 0.6 to 1.2 cm so that it can be received in the shoe or orthotic without obstruction. A fabric or elastomer bellows 20 extends around the space between the upper and lower plates 12, 14 to enclose the active member 18 and prevent dirt or obstructions to stop its indicating function. Apertures may be provided in the member 20 to permit the flow of air or if fabric is used, the porosity of fabric is sufficient. This also helps dampen the action of the snap so that it is not overly violent. In any case, when more than the permitted weight is exerted by the user's heel on the device 10, it will snap into its unstable position of FIG. 2B giving a very clear tactile and in this case, audible signal to the user to take a less forceful next step. As soon as pressure is removed from the device, it returns to its stable position of FIG. 1.

As noted above, no power source is needed and the invention automatically resets.

Figure 3:
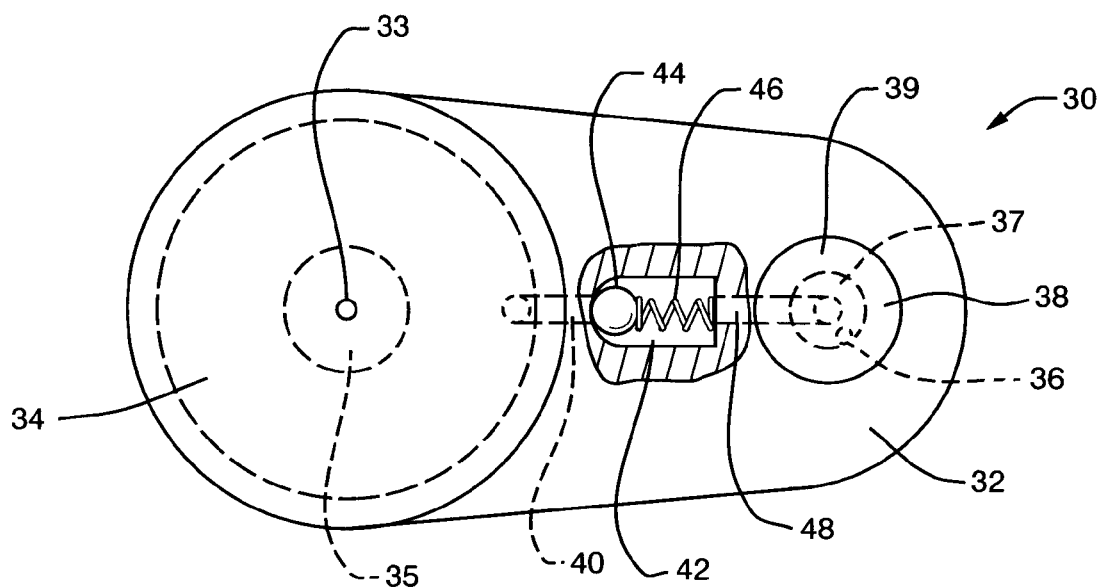
FIG. 3 is a top plan view of a second embodiment of the invention.
Figure 4:
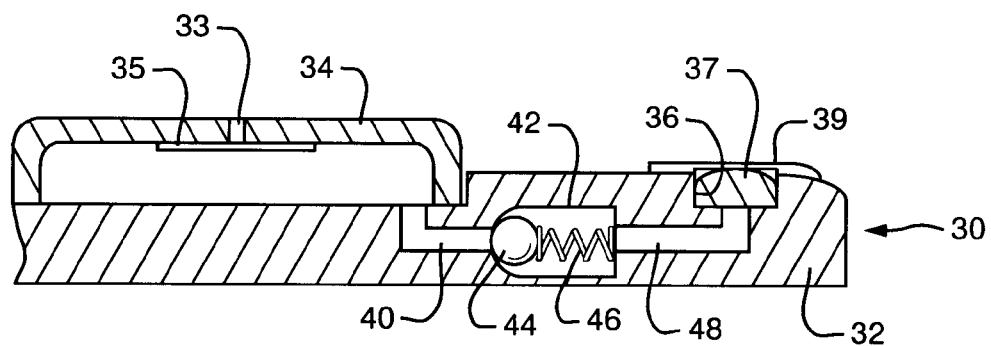
FIG. 4 is a side sectional view of the embodiment of FIG. 3.

A second embodiment of the invention is illustrated in FIGS. 3 and 4.

In FIG. 3, the mechanical indicator of the present invention is designated 30 and comprises a flexible air cavity member 34 into which air can flow through a one-way valve, consisting of a small centrally-located hole 33 covered with an elastomeric patch 35. As best shown in FIG. 4, the weight bearing indicator body 32 contains an air conduit 40 that channels pressurized air from the compressed air cavity 34 through a one-way check valve arrangement 42, 44, 46 through another conduit 48, and finally into a rigid cavity 36. As a result, a piston 37 is forced upwards because of the increase in air pressure. Cavity member 34 can be made of urethane or neoprene.

With the second embodiment of the invention in contact with the bottom of a patient's foot, their heel compresses the flexible air cavity member 34 with each step of the injured extremity. Air is not allowed to exit the centrally-located hole 33 because of an elastomeric patch 35 attached to the inside of the air cavity member 34 that acts as a one-way valve (a.k.a. flapper valve). When the patient's heel is not pushing down on the air cavity member 34, this cavity can re-inflate (in case air escapes through air conduit 40) because air can enter through hole 33, and due to the resilience of the cap or dome that forms cavity member 34.

When the air pressure that builds up in the compressed cavity member 34 reaches a certain level corresponding to the weight limit for that patient, air in conduit 40 pushes on a one-way, force actuated valve (check valve) consisting of sealing ball 44 that is held in place at the outlet of conduit 40 by a pre-compressed coil spring 46. The spring 46 and ball 44 are contained within cavity 42. The threshold pressure level in the cavity 34 is controlled by the compression force of the spring 46 on the ball 44. In other words, the stiffness and pre-compression of spring 46 dictate the force level at which the patient is indicated. Escaping air from conduit 40 passes through conduits 42 and 48.

The build-up of air pressure in cavity 36 pushes piston 37 up into the bottom the patient's foot indicating that the weight limit has been exceeded. The pressurized air in cavity 36 is allowed to eventually escape outside the device 30 because of a small gap between the outer diameter of the piston 37 and the inner diameter of the cavity 36. After the pressurized air eventually escapes around the piston 37, a porous, elastic membrane 39 returns the piston back to its original position.

The flexible air cavity member 34 is advantageously between 4 and 6 cm in diameter to conveniently fit within the shoe, and with the overall height of the device as shown in FIG. 4, being between 0.6 and 1.2 cm.

Figure 5:
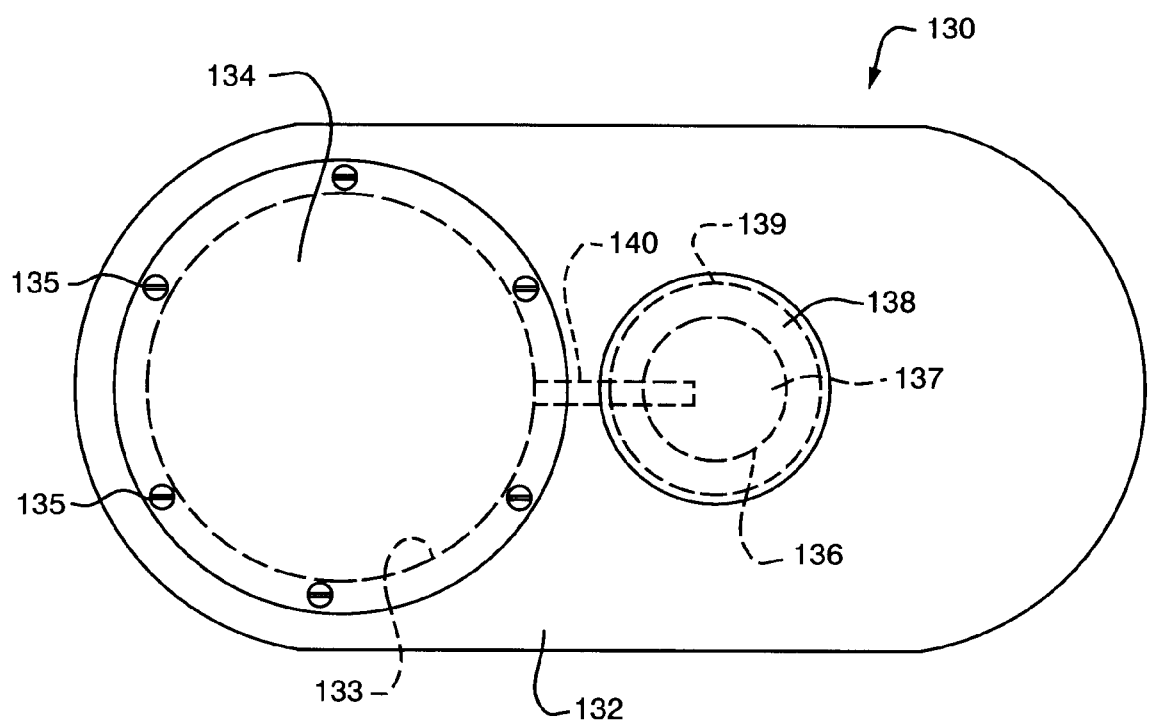
FIG. 5 is a top plan view of a third embodiment of the invention.
Figure 6:
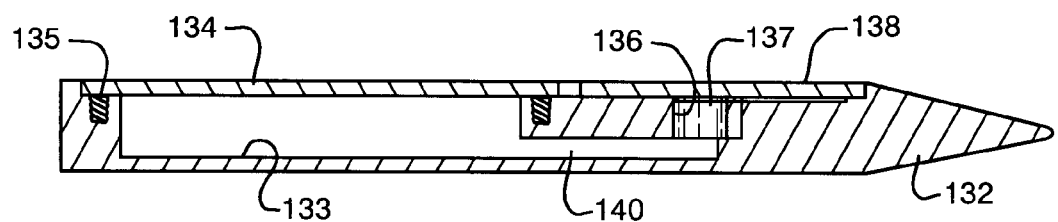
FIG. 6 is a side sectional view of the embodiment of FIG. 5.

In FIGS. 5 and 6, the mechanical indicator of a third embodiment of the present invention is generally designated 130 and comprises a reaction plate 132 made, for example, of plastic and shaped to fit inside the heel and arch area of a shoe. As best shown in FIG. 6, a cylindrical cavity 133 is defined in the reaction plate 132 in the heel area. Cavity 133 is covered by an actuator plate 134 which closes the cavity in an air tight manner and is fastened, for example, by a plurality of screws 135. At a location space from cavity 133, a second cavity 136 is formed, this cavity being cylindrical and slidably receiving a piston 137 for up and down movement in cavity 136.

A flexible film 138 is attached to the upper surface of plate 132 and extends over the top of piston 137. Film 138 is made of rubber or other flexible material so that when piston 137 rises, it also pushes film 138 upwardly and into engagement with the instep of the wearer's foot. Film 138 may be attached to plate 132 only around its perimeter shown at 139 in FIG. 5, to allow free movement of the central part of the film.

A connecting conduit 40 communicates the interior of cavity 133 with the interior of cavity 137.

The heel plate 134 is selected to have enough flexibility so that when it receives a force greater than the selected amount of weight permitted for the patient, it collapses partly into cavity 133, displacing some of the air through connecting conduit 140 and up under piston 137 in cavity 136, moving the piston upwardly and thus deforming film 138 up into the instep of the wearer indicating that too much force has been applied. Rather than being a step-wise indication as in the embodiments of FIGS. 1 and 3, the indication of the embodiment of FIGS. 5 and 6 is more continuous with a greater feedback signal being generated for greater force beyond the selected force.

The selected weight is adjusted by selecting the material and thickness of plate 134. Screws 135 which produce the air tight seal between the plate 134 and the plate 132, also permit the actuator plate 134 to be removed and exchanged with another plate as the patient is able to exert more weight on the recovering extremity.

Also, by varying the thickness and material of plate 134, the device can be adapted to users of different sizes and weights and even for use by children. For example, an orthopedic patient typically varies the amount of body weight supported from 25 to 75% of total body weight. It is estimated that the heel plate thickness will vary between 1.5 and 3 mm when material like nylon is used for low to medium adult loads. Polycarbonate of the same thickness can be used for medium to high adult loads with polypropylene used for most children's loads and high density polyethylene for low children's loads. Heel plate 134 is also advantageously between 4 and 6 cm in diameter to conveniently fit within the shoe, and with the overall height of the device as shown in FIG. 6, being between about 0.6 and 1.2 mm.

While a specific embodiment of the invention has been shown and described in detail to illustrate the application of the principles of the invention, it will be understood that the invention may be embodied otherwise without departing from such principles.

What is claimed:

1. A non-electric mechanical weight bearing indicator assembly for producing a tactile signal to a foot of a user when the user applies more than a selected amount of weight on the user foot to avoid damaging the user foot, comprising:

a foot covering covering the foot of the user, the foot covering having a weight bearing surface; and a non-electric, mechanical indicator in the foot covering at a location to be between the user foot and the weight bearing surface, when the user wears the foot covering, the indicator comprising:

a reaction plate for receiving force from the weight bearing surface;

an actuator plate mounted for movement to said reaction plate for receiving force from the foot of a user wearing the foot covering; and a convex disk having a perimeter in contact with one of the reaction plate and the actuator plate, and a peak engaged with the other of the reaction plate and the actuator plate, the disk having an unstable, snap-through, concave position when more than the selected amount of weight is exerted on the disk through the actuator plate to generate a tactile signal to the user to signal to the user that more than the selected amount of weight has been applied to the disk, the disk automatically returning to a stable convex condition when less than the selected amount of weight is exerted on the disk.

* * * * *